United States Patent
Haney

(10) Patent No.: US 8,720,287 B2
(45) Date of Patent: May 13, 2014

(54) GAS TRAP

(76) Inventor: Perry Haney, Tahoka, TX (US)

(*) Notice: Subject to any disclaimer, the term of this patent is extended or adjusted under 35 U.S.C. 154(b) by 328 days.

(21) Appl. No.: 13/337,035

(22) Filed: Dec. 23, 2011

(65) Prior Publication Data

US 2012/0325025 A1 Dec. 27, 2012

Related U.S. Application Data

(60) Provisional application No. 61/457,280, filed on Feb. 17, 2011.

(51) Int. Cl.
*G01N 1/22* (2006.01)
*B01D 19/00* (2006.01)

(52) U.S. Cl.
USPC .............. 73/863.41; 73/863.21; 73/863.51; 702/6; 702/9; 702/11

(58) Field of Classification Search
USPC ............. 73/863.21, 863.22, 863.41, 863.51; 702/6, 9, 11
See application file for complete search history.

(56) References Cited

U.S. PATENT DOCUMENTS

| | | | | |
|---|---|---|---|---|
| 2,447,595 A * | 8/1948 | Pigott et al. | | 73/863.43 |
| 3,635,092 A * | 1/1972 | Maughan et al. | | 73/864.62 |
| 3,699,814 A * | 10/1972 | Kaufman | | 73/863.11 |
| 3,817,100 A * | 6/1974 | Anderson et al. | | 73/861.63 |
| 3,884,081 A * | 5/1975 | Griffith | | 73/863.31 |
| 4,040,299 A * | 8/1977 | Snyder | | 73/864.52 |
| 4,272,258 A * | 6/1981 | Shifflett | | 95/260 |
| 4,358,298 A * | 11/1982 | Ratcliff | | 96/189 |
| 4,367,078 A * | 1/1983 | Hendrix | | 96/189 |
| 5,161,417 A * | 11/1992 | Strong et al. | | 73/863.86 |
| 5,199,509 A * | 4/1993 | Wright et al. | | 175/50 |
| 5,621,180 A * | 4/1997 | Simon et al. | | 73/864.52 |
| 5,902,378 A * | 5/1999 | Obrejanu | | 95/248 |
| 7,350,536 B2 * | 4/2008 | Evans | | 137/315.17 |
| 7,655,079 B2 * | 2/2010 | Lai et al. | | 96/216 |
| 7,957,903 B1 * | 6/2011 | Selman et al. | | 702/6 |
| 2005/0132889 A1* | 6/2005 | MacDuff | | 96/165 |
| 2008/0047370 A1* | 2/2008 | Vickery, Jr. | | 73/863.21 |
| 2009/0136298 A1* | 5/2009 | Augenstein et al. | | 405/129.85 |
| 2012/0000278 A1* | 1/2012 | Phillips | | 73/152.04 |
| 2013/0042666 A1* | 2/2013 | Santucci et al. | | 73/19.07 |
| 2013/0275047 A1* | 10/2013 | Selman et al. | | 702/9 |

\* cited by examiner

*Primary Examiner* — David A Rogers
(74) *Attorney, Agent, or Firm* — Norred Law, PLLC; Warren V. Norred

(57) ABSTRACT

The gas trap collects formation gases from oil well fluid flow in real time. Gases are released by the fluid when agitated by an agitating pipe which stirs the fluid flow; the gases are then collected and separated from the fluid to be analyzed. The gas trap does hinder the flow of formation cuttings in the drilling fluid flow line, but allows the formation cuttings to flow around the agitator pipe and out to the sample box.

11 Claims, 2 Drawing Sheets

GAS TRAP

CROSS-REFERENCES TO RELATED APPLICATIONS

Figure 1:
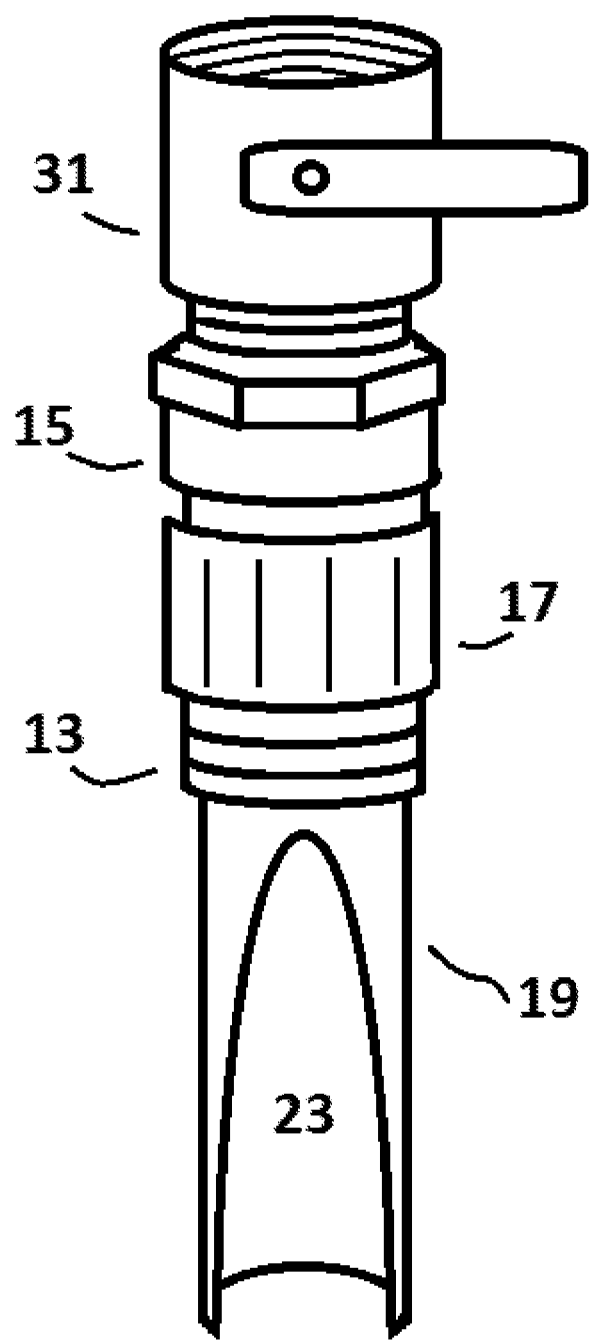

Provisional Patent 61/457,280, filed Feb. 17, 2011.

STATEMENT REGARDING FEDERALLY SPONSORED RESEARCH AND DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION

1. Field of the Invention

The invention pertains to the collection of formation gases to be analyzed as oil wells are drilled.

2. Background Art

The oil and gas industry has always treated the collection of formation gas and formation cuttings data as one function. On an oil and gas drilling project, there are two different applications. The first drilling application is the collection of formation gases and cuttings while the drilling fluid is directed to the reserve pits. The second drilling application is the collection of formation gases and cuttings while the drilling mud is directed to the steel pits.

The traditional configuration begins at the well head. From the well head, there is a flow line in which the drilling fluid leaves the well bore. The flow line is commonly six or eight inches in diameter. The flow line extends from the well head out towards the steel and reserve pits, where there are control valves that control the direction of the drilling fluid, either to the reserve pits, or to the steel pits. The reserve pits are located further away from the well bore and behind the steel pits. The drilling fluid from the well head carries the formation gases and formation cuttings from the well bore, to either the reserve pits, or the steel pits. The formation cuttings are dumped into the reserve pits, where they cannot reenter the drilling system. The formation gases are either released into the atmosphere, or flared off. The drilling fluid is then circulated around into the well bore, where the process is restarted.

Drilling Phase One—Water/Reserve Pits—At the beginning of a drilling project, the drilling fluid is either fresh water or brine water. The drilling fluid is bypassed the steel pits and out to the reserve pits, which are located behind the steel pits. The reserve pits are earth dug pits, in the shape of a horseshoe and at a slight angle. This allows the formation cuttings to be dropped out of the fluid. The fluid flows around to the other end of the horseshoe where it is suctioned back into the well bore. The flow line is an open ended system, so there is not any pressure on the flow line. The flow line is filled approximately halfway with drilling fluid. The drilling fluid is a mixture of formation gases and formation cuttings. The top half of the flow line is filled with formation gases.

Current practice in the industry is to insert a two-inch line into the flow of drilling mud, diverting it to the formation cuttings sample box that is installed near the end of the drilling fluid flow line and installed low enough, relative to the drilling mud source, so the fluid flows easily into the formation sample box.

The formation cutting sample box is a rectangular box, with a sliding door in the front. The formation cutting sample box is designed for catching formation cuttings, as well as holding enough drilling fluid for the agitator, for monitoring formation gas. Its width and length must be wide enough, to allow a sample box agitator stand to fit inside, and long enough, as not to hinder the collection of formation cuttings to be analyzed. It must also be built sturdy enough to withstand the vibration from the agitating motor, as well as the combined weight of the agitating stand and motor. The sliding door has a handle cut along its top edge. The handle is to allow excess fluid to flow out of the sample box, out into the reserve pits and not over the sides or end of the sample box. The sliding door is also used for washing formation cuttings out into the reserve pits, after a sample is collected, so that the next ten foot sample can be caught inside the sample box.

The sample box agitating stand is a steel stand about three to four feet tall, onto which the agitator motor is mounted. The stand has an entrance and exit portal in it that allows drilling fluid to enter and leave the box. An explosion-proof electrical agitator motor is mounted on the box which rotates beaters affixed to the motor's rotating shaft. A suction hole is drilled in the sample box to allow formation gases to be sucked out of the sample box to be analyzed.

Drilling Phase Two—Mudding Up/Steel Pits—At some point in the drilling process, the crews will begin to "mud up", a term used by the oil and gas industry to describe the process of adding chemicals to the drilling fluid to control the properties of the drilling mud. At this point, the drilling fluid is now referred to as drilling mud. Once the determination has been made to start mudding up, the two valves are turned in the drilling fluid flow line and the flow is diverted from the reserve pits to the steel pits. Then chemicals are mixed to start the mudding up process. The drilling mud is directed to the steel pits to: 1) begin the mudding up process, 2) prevent loss of expensive drilling mud, 3) to maintain, control, and change the properties of the drilling mud, 4) to protect the well bore, and 5) to prevent or control lost circulation.

During the second phase, when drilling mud is used, the agitator stand is placed inside the sample box, at a lower bottom of a large vat, known as the possum belly, located in front of the shaker. The drilling fluid flow line enters into the possum belly at its base. The drilling mud fills the possum belly, until the drilling mud spills over the front edge, onto the shaker. The shaker includes screens and vibrates very rapidly. The drilling mud and formation cuttings spill onto the screens. The vibration of the shaker allows the drilling mud to fall through the screens, into the steel pits, leaving the formation cuttings on the screens. The drilling mud is remixed and suctioned back into the well bore. The formation cuttings are vibrated to the end of the shaker where they fall onto a slide. A sample of the formation cuttings is collected off the slide for examination. Formation gases are collected for monitoring at the possum belly. The remainder is washed off the slide, into the reserve pits.

The traditional method beats gases trapped out of the drilling fluid that is collected in the sample box, and only those gases. The sample box has to be moved when the drilling starts the mudding up process. The gas in the top half of the drilling fluid flow line simply escapes into the atmosphere and is never analyzed. Formation cuttings fill the formation cuttings sample box, plugging the hole at the base of the agitator bracket, and cause improper formation gas readings. The end result is that formation gases either cannot be monitored at all, or have very inaccurate readings. The traditional method also uses an agitating motor that vibrates, rusts, and requires electrical power in an outdoor installation. In such an environment, loss of power or a rusted motor renders the sampling system unusable.

The oil industry needs to be able to more efficiently sample the gases coming up out of the well with the drilling fluid.

BRIEF SUMMARY OF THE INVENTION

The invention allows for the collection of formation gases by placement of an agitating pipe directly in the drilling fluid flow line; the pipe's opening cut at an angle so gas in the top half of the drilling fluid flow line (where there is no drilling fluid) will be collected and also analyzed, along with the gas agitated from the drilling fluid. Because of the design of the gas trap of the invention, formation cuttings will not plug up the gas trap, but flow around the agitator pipe and out to the sample box. As long as circulation is maintained, formation gas readings are maintained with the gas trap of the invention. No electricity or moving parts are used, eliminating issues associated with rusty motors and electrical power sourcing.

BRIEF DESCRIPTION OF THE SEVERAL VIEWS OF THE DRAWING(S)

Exemplary embodiments of the gas trap are set forth in the figures below.

FIG. 1—Exploded Orthogonal view of the Agitating Pipe with Ball Valve.

Figure 2:
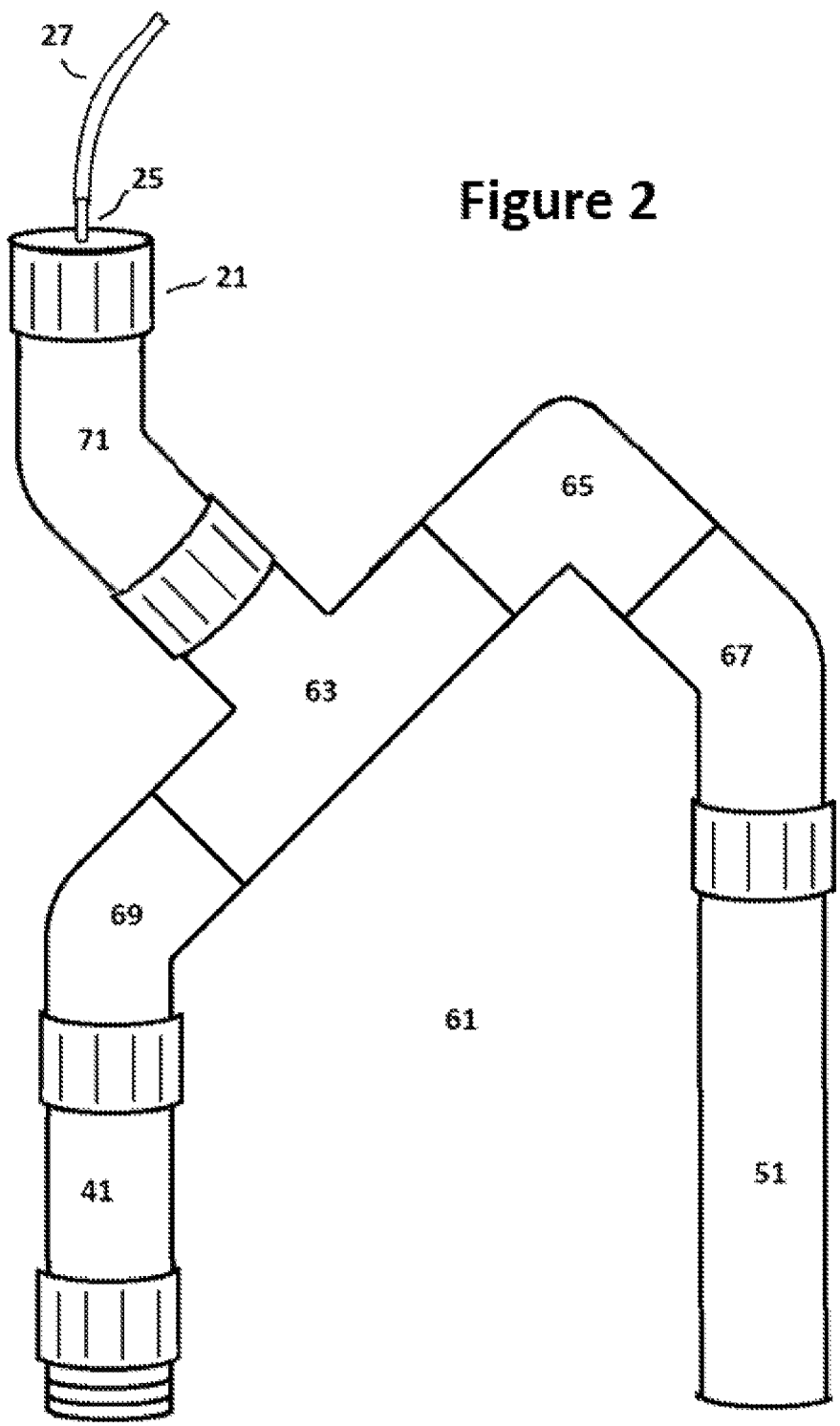

FIG. 2—Plan view of the Spillway with Short Stack, Expansion Chamber, Collection Cap, and Long Stack.

DETAILED DESCRIPTION OF THE INVENTION

Aspects of the present invention are disclosed in the following description and related figures directed to specific embodiments of the invention. Those skilled in the art will recognize that alternate embodiments may be devised without departing from the spirit or the scope of the claims. Further, the description and figures used herein should be viewed only as exemplary in nature. It can be appreciated that the exemplary embodiments described herein may include descriptions that related to specific sizes, shapes or types of material; however the methods, apparatuses and systems described herein are not limited to these particular sizes, shapes and types of materials. Instead, it may be appreciated that any desired materials may be utilized to form the methods, apparatuses and systems so as to achieve any desired results. Additionally, well-known elements of exemplary embodiments of the invention will not be described in detail or will be omitted so as not to obscure the relevant details of the invention.

As used herein the word "exemplary" means "serving as an example, instance or illustration." The embodiments described herein are not limiting, but rather are exemplary only. It should be understood that the described embodiments are not necessarily to be construed as preferred or advantageous over other embodiments. For example, the description below discusses PVC, the common abbreviation for polyvinyl chloride, a popular thermoplastic polymer, that is used to construct the invention, but many other materials can be used.

As shown in FIGS. 1 and 2, the Gas Trap is typically constructed using 2" PVC or other suitable materials, comprising an Agitating Pipe 19 and Collection Cap, 21. Optional components include a Ball Valve 31, Short Stack 41, Long Stack 51, Spillway 61, and Extension Gas Chamber 71, as needed. Each is explained below.

As shown in FIG. 1, the Agitating Pipe Subassembly comprises two male Couplings 13, 15, with a Nipple 17 between them, and an Agitating Pipe 19 attached to the lower Coupling 13. In FIG. 1, an optional Ball Valve 31 is used. As shown in the figures, the Agitating Pipe 19 is a piece of pipe cut to a length that is close to the inside diameter of the drilling fluid flow line, and cut to an angle that makes the agitating pipe's Collection Opening 23 inside the flow line pipe as large as possible, extending into the fluid flowing through the flow line pipe, but not colliding with the opposite inside side of the flow line pipe as the Agitating Pipe 19 is installed. The angle is determined by the length of the pipe. The Agitating Pipe 19 is cut and attached to a Coupling 13, which mounts onto the wall of the fluid flow line. The Agitating Pipe 19 is installed with the angled Collection Opening 23 so it faces the flow of the drilling fluid or mud, so when the fluid reaches the Agitating Pipe 19, the fluid is agitated and gas is released from the flow material. This gas adds to the presence of gases already present in the flow line, all of which flows into the Collection Opening 23, travels through the Agitating Pipe 19, into the Collection Cap 23 (FIG. 2) and then goes through the Sample Tube 27 (FIG. 2) to the test equipment that analyzes the gas.

As shown in FIG. 2, the Collection Cap 21 is a two-inch PVC threaded cap with a barbed hose Adaptor 25 screwed into its center. A flexible Sample Tube 27 slips over the Adaptor 25. Formation gases leave the Gas Trap through the Sample Tube 27 and into the testing apparatus (not part of the invention).

As shown in FIG. 1, an optional Ball Valve 31 may be installed on the Agitating Pipe 19 for the convenience to the operators, and not necessary to the invention, but very helpful to operators.

As shown in FIG. 2, an optional Short Stack 41, comprising a length of PVC pipe with a male coupling affixed to one end and a female coupling on the other, may be installed between the Agitating Pipe 19 and Collection Cap 21 to prevent drilling fluid that might otherwise be drawn into the Collection Cap 21, or used between the Agitating Pipe 19 and Spillway 61 assembly. The actual length of the pipe can vary to whatever length is necessary to prevent the fluid from reaching the Collection Cap 21.

As shown in FIG. 2, the Spillway 61 is a PVC pipe subassembly installed on the top opening of the Agitating Pipe 19. Its purpose is to further allow gases within the drilling fluid to separate from the fluid inside the Agitating Pipe, prevent the Collection Cap 21 from being clogged with drilling fluid, and to allow an escape of the fluid from the Agitating Pipe 19. It can be constructed in many different ways, but is currently configured with a PVC Female Tee 63, with a Collection Cap 21 mounted on the side opening, and the main line connection of the Tee 63 attached to the Agitating Pipe 19 through a 45° Coupling 69 on one side, and a drilling fluid discharge route wherein the fluid flows through the Female Tee 63, an Elbow 65, and 45° Discharge Coupling 67 and optional Long Stack 51 drilling mud exit pipe mounted on the other side.

Shown in FIG. 2, the Extension Gas Chamber 71 is an optional component length of pipe added between the Tee 63 of the Spillway Assembly 61 and the Collection Cup 21 to reduce the danger that drilling mud may be drawn into the Collection Cup 21.

Shown in FIG. 2, an optional Long Stack 51 is an added length of pipe used as an extension on the end of the Spillway, affixed to the open end of the 45° male coupling to prevent splashing of the drilling mud when the drilling mud is directed into the possum belly. It is also used in the sample box to prevent splashing of the drilling mud, when catching formation samples while the possum belly is being bypassed.

The invention can be made with many different configurations. The specific discussion and explanation above is not intended to be a limiting description of the invention, but merely one embodiment as the invention is currently constructed.

The invention claimed is:

1. An apparatus used to collect gas samples from a fluid line in which a mixture of liquids and gases may be flowing, comprising:
   a) an Agitating Pipe—A pipe installed perpendicular to the fluid line wall, in which the interior end of the pipe is cut at an angle and length to fit inside the diameter of the pipe, and the installed pipe is set so that it faces into the fluid flow;
   b) a Male Coupling—A male coupling into which the Agitating Pipe is attached, and which screws into a fluid line, holding the Agitating Pipe in place;
   c) a Collection Cap—A threaded cap with a hose adaptor installed in its middle which is installed in the top of the Agitating Pipe.

2. An apparatus as in claim 1, in which an additional length of pipe is installed between the Agitating Pipe and Collection Cap, raising the vertical height of the Collection Cap from the fluid line.

3. An apparatus as in claim 1, in which a Ball Valve is connected between the Agitating Pipe and the Collecting Cap.

4. An apparatus as in claim 1, with an additional Spillway subassembly, comprising:
   a) a 45° Coupling—installed into the top of the Agitating Pipe;
   b) a "Tee"—installed with a main line port of the Tee connected into the top of the 45° Coupling, and the Collection Cap is installed on the Tee's middle opening, and the Tee oriented as vertical as possible;
   c) a 90° Elbow—installed with one end in the top port of the Tee, and the other end pointing as downward as possible;
   d) a 45° Discharge Coupling—installed into the 90° Elbow such that it directs discharge in a direction desired by the operator.

5. An apparatus as in claim 4 in which an additional length of pipe is added after the 45° Discharge Coupling, lowering the height at which any discharged fluid is released.

6. An apparatus as in claim 4, in which an additional length of pipe is added between the Spillway's Tee and the Collection Cap.

7. A method of collecting gas samples from a mixture of fluid and gas in a flow line, comprising:
   a) cutting a section of pipe at an angle on one end;
   b) installing the cut pipe into a male coupling;
   c) screwing the male coupling into an opening in a threaded hole in a flow line such that the cut pipe faces toward the flow of materials;
   d) affixing a pipe cap into the top end of the pipe assembly;
   e) installing a barbed hose adaptor in the middle of the pipe cap;
   f) attaching one end of a sample tube to the pipe cap, and one end to the test analysis equipment.

8. The method as in claim 7, adding an additional step of installing a ball valve between the male coupling and the pipe cap.

9. The method as in claim 7, adding an additional step of installing a ball valve between the male coupling and the pipe cap.

10. A method as in claim 7, also comprising the installation of an additional pipe length to raise the pipe cap higher in relation to the flow line.

11. A method of collecting gas samples from a fluid and gas mixture in a flow line, comprising:
   a) cutting a section of pipe at an angle on one end;
   b) installing the un-angled end of the pipe into a male coupling;
   c) screwing the male coupling into an opening in a threaded hole in a flow line such that the angled end of the cut pipe extends into the flow line to be sampled, with the pipe turned so the opening formed by the angled cut faces the flow of materials;
   d) attaching a 45° coupling to the top of the male coupling on the outside of the flow line;
   e) installing a main line port of a tee onto the 45° coupling; with the tee oriented as vertical as possible;
   f) installing a cap on the tee's side port;
   g) installing a barbed hose adaptor in the middle of the pipe cap;
   h) installing a 90° elbow to the top main line port of the tee, pointing the open end of the elbow as downward as possible;
   i) affixing a 45° male coupling to the a 90° elbow, orienting the coupling so it directs discharge from the pipe in an operator-desired direction;
   j) attaching one end of a sampling tube to the barbed hose adaptor in the pipe cap, and one end to the test analysis equipment;
   k) adding an additional length of pipe between the side port of the tee and the pipe cap if flow of material through the flow line rises to clog the sampling tube; and
   l) adding an additional length of pipe to the discharge-directing 45° male coupling and positioning it to direct discharge to a desired location when the discharge flow does not land where the operator otherwise desires.

* * * * *